(12) United States Patent
Huddleston

(10) Patent No.: US 11,678,980 B2
(45) Date of Patent: Jun. 20, 2023

(54) FULLY-TRANSSEPTAL APICAL PAD WITH PULLEY FOR TENSIONING

(71) Applicant: Tendyne Holdings, Inc., St. Paul, MN (US)

(72) Inventor: Preston James Huddleston, Maplewood, MN (US)

(73) Assignee: Tendyne Holdings, Inc., St. Paul, MN (US)

(*) Notice: Subject to any disclaimer, the term of this patent is extended or adjusted under 35 U.S.C. 154(b) by 188 days.

(21) Appl. No.: 17/371,584

(22) Filed: Jul. 9, 2021

(65) Prior Publication Data

US 2022/0054258 A1 Feb. 24, 2022

Related U.S. Application Data

(60) Provisional application No. 63/067,538, filed on Aug. 19, 2020.

(51) Int. Cl.
*A61F 2/24* (2006.01)

(52) U.S. Cl.
CPC ............ *A61F 2/2418* (2013.01); *A61F 2/243* (2013.01); *A61F 2210/0014* (2013.01); *A61F 2250/0051* (2013.01)

(58) Field of Classification Search
CPC .......... A61F 2/24; A61F 2/2427; A61F 2/243; A61F 2/2433; A61F 2/2451; A61F 2/2454; A61F 2/2457; A61F 2/2478; A61F 2/2436; A61F 2/246; A61F 2220/0008; A61F 2/2439; A61F 2/9517; A61F 2/9522; A61F 2/95; A61F 2/2418
See application file for complete search history.

(56) References Cited

U.S. PATENT DOCUMENTS

| | | | |
|---|---|---|---|
| 2,697,008 | A | 12/1954 | Ross |
| 3,409,013 | A | 11/1968 | Berry |
| 3,472,230 | A | 10/1969 | Fogarty et al. |
| 3,476,101 | A | 11/1969 | Ross |
| 3,548,417 | A | 12/1970 | Kischer |

(Continued)

FOREIGN PATENT DOCUMENTS

| | | |
|---|---|---|
| CN | 1486161 A | 3/2004 |
| CN | 1961845 A | 5/2007 |

(Continued)

OTHER PUBLICATIONS

US 9,155,620 B2, 10/2015, Gross et al. (withdrawn)

(Continued)

*Primary Examiner* — Seema Mathew
(74) *Attorney, Agent, or Firm* — Sleman & Lund LLP

(57) ABSTRACT

An apical pad for securing a prosthetic heart valve within a native valve annulus. The apical pad includes a first collar, a second collar and plurality of struts extending between the first collar and the second collar. The plurality of struts has a delivery condition in which the plurality of struts collectively form a first cross-section and a deployed condition in which the plurality of struts collectively form a second cross-section greater than the first cross-section. The apical pad may be coupled to a tether extending from a prosthetic heart valve and may transition from the delivery condition to the deployed condition by tensioning the tether.

12 Claims, 9 Drawing Sheets

(56) References Cited

U.S. PATENT DOCUMENTS

| | | |
|---|---|---|
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Fhuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |

(56) References Cited

U.S. PATENT DOCUMENTS

| | | |
|---|---|---|
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,361,137 B2 | 4/2008 | Taylor et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,618,449 B2 | 11/2009 | Tremulis et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,783,366 B1 | 8/2010 | Morgan et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |

(56) References Cited

U.S. PATENT DOCUMENTS

| | | |
|---|---|---|
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,556,963 B2 | 10/2013 | Tremulis et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,961,597 B2 | 2/2015 | Subramanian et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,468,526 B2 | 10/2016 | Subramanian et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,848,880 B2 | 12/2017 | Coleman et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,016,271 B2 | 7/2018 | Morriss et al. |
| 10,226,334 B2 | 3/2019 | Rowe et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0069593 A1 | 4/2003 | Tremulis et al. |
| 2003/0078652 A1 | 4/2003 | Sutherland |
| 2003/0100939 A1 | 5/2003 | Yodat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049211 A1 | 3/2004 | Tremulis et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0210304 A1 | 10/2004 | Seguin et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251157 A1 | 11/2005 | Saadat et al. |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |

(56) References Cited

U.S. PATENT DOCUMENTS

| | | |
|---|---|---|
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0074397 A1 | 4/2006 | Shimada |
| 2006/0074484 A1 | 4/2006 | Huber |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0196137 A1 | 9/2006 | Brenzel et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Rahdert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0173931 A1 | 7/2007 | Tremulis et al. |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1* | 11/2007 | Solem .................. A61F 2/2466 |
| | | 606/151 |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0109069 A1 | 5/2008 | Coleman et al. |
| 2008/0114442 A1 | 5/2008 | Mitchell et al. |
| 2008/0125861 A1* | 5/2008 | Webler ................ A61B 17/064 |
| | | 623/2.36 |
| 2008/0140189 A1 | 6/2008 | Nguyen et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0228223 A1* | 9/2008 | Alkhatib ............ A61B 17/0401 |
| | | 606/221 |
| 2008/0228263 A1 | 9/2008 | Ryan |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2008/0300678 A1 | 12/2008 | Eidenschink et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0076600 A1* | 3/2009 | Quinn ............... A61B 17/00234 |
| | | 623/2.34 |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0182417 A1 | 7/2009 | Tremulis et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276038 A1 | 11/2009 | Tremulis et al. |
| 2009/0276040 A1* | 11/2009 | Rowe ..................... A61F 2/90 |
| | | 623/2.18 |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0004740 A1 | 1/2010 | Seguin et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |

(56) References Cited

U.S. PATENT DOCUMENTS

| | | |
|---|---|---|
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0121435 A1 | 5/2010 | Subramanian et al. |
| 2010/0121437 A1 | 5/2010 | Subramanian et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280589 A1 | 11/2010 | Styrc |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0022157 A1 | 1/2011 | Essinger et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0213459 A1 | 9/2011 | Garrison et al. |
| 2011/0218619 A1 | 9/2011 | Benichou et al. |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0010700 A1 | 1/2012 | Spenser |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0109079 A1 | 5/2012 | Asleson et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0245678 A1 | 9/2012 | Solem |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0103140 A1 | 4/2013 | Subramanian et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0226290 A1 | 8/2013 | Yellin et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0304200 A1 | 11/2013 | McLean et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1* | 12/2013 | Khalil .................. A61F 2/2427 623/2.11 |
| 2013/0338752 A1 | 12/2013 | Geusen et al. |
| 2013/0338764 A1 | 12/2013 | Thornton et al. |
| 2014/0005778 A1 | 1/2014 | Buchbinder et al. |
| 2014/0031924 A1 | 1/2014 | Bruchman et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243857 A1 | 8/2014 | Miller et al. |
| 2014/0243965 A1 | 8/2014 | Benson et al. |
| 2014/0243966 A1 | 8/2014 | Garde et al. |
| 2014/0257466 A1 | 9/2014 | Board et al. |
| 2014/0277419 A1 | 9/2014 | Garde et al. |
| 2014/0296969 A1 | 10/2014 | Tegels et al. |
| 2014/0296970 A1* | 10/2014 | Ekvall .................. A61F 2/2436 623/2.11 |
| 2014/0296971 A1 | 10/2014 | Tegels et al. |
| 2014/0296972 A1* | 10/2014 | Tegels .................. A61F 2/2436 623/2.11 |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358222 A1 | 12/2014 | Gorman, III et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1* | 1/2015 | Vidlund ................ A61F 2/2412 623/2.14 |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1* | 5/2015 | Coleman .......... A61B 17/12109 623/2.11 |
| 2015/0142103 A1* | 5/2015 | Vidlund ................ A61F 2/2418 623/2.17 |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |

(56) References Cited

U.S. PATENT DOCUMENTS

| | | |
|---|---|---|
| 2015/0216660 A1 | 8/2015 | Pintor |
| 2015/0223820 A1 | 8/2015 | Olson |
| 2015/0223934 A1* | 8/2015 | Vidlund ............ A61B 17/0401 623/2.11 |
| 2015/0223935 A1 | 8/2015 | Subramanian et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0342737 A1* | 12/2015 | Biancucci ............ A61F 2/2466 600/37 |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1* | 1/2016 | Christianson ......... A61F 2/2418 623/2.11 |
| 2016/0022448 A1* | 1/2016 | Tobis .................. A61F 2/88 623/1.36 |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0120673 A1 | 5/2016 | Siegel et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0074160 A1* | 3/2017 | Thomassin ............ F02B 55/16 |
| 2017/0079790 A1* | 3/2017 | Vidlund ............ A61B 17/0401 |
| 2017/0100245 A1 | 4/2017 | Subramanian et al. |
| 2017/0100248 A1 | 4/2017 | Tegels et al. |
| 2017/0128208 A1 | 5/2017 | Christianson et al. |
| 2017/0181854 A1 | 6/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1* | 10/2017 | Christianson ......... A61F 2/2439 |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2017/0325842 A1 | 11/2017 | Siegel |
| 2018/0028314 A1 | 2/2018 | Ekvall et al. |
| 2018/0078368 A1 | 3/2018 | Vidlund et al. |
| 2018/0078370 A1* | 3/2018 | Kovalsky ............ A61F 2/2433 |
| 2018/0147055 A1 | 5/2018 | Vidlund et al. |
| 2018/0193138 A1 | 7/2018 | Vidlund |
| 2018/0296212 A1 | 10/2018 | Jimenez et al. |
| 2019/0125533 A1* | 5/2019 | Vidlund ............ A61F 2/2436 |
| 2019/0167407 A1 | 6/2019 | Schaer et al. |
| 2020/0179111 A1 | 6/2020 | Vidlund et al. |
| 2020/0205968 A1* | 7/2020 | Vidlund ............ A61F 2/2418 |
| 2021/0022855 A1* | 1/2021 | Tegels ............ A61F 2/2418 |
| 2022/0015899 A1* | 1/2022 | Huddleston ......... A61F 2/2418 |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101861134 A | 10/2010 |
| CN | 101984938 A | 3/2011 |
| CN | 102791223 A | 11/2012 |
| CN | 102869317 A | 1/2013 |
| CN | 102869318 A | 1/2013 |
| CN | 102869321 A | 1/2013 |
| CN | 103220993 A | 7/2013 |
| CN | 103974674 A | 8/2014 |
| CN | 102639179 B | 10/2014 |
| DE | 2246526 A1 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2010517623 A | 5/2010 |
| JP | 2013512765 A | 4/2013 |
| JP | 2014532457 A | 12/2014 |
| NL | 1017275 C2 | 8/2002 |
| SU | 1271508 A1 | 11/1986 |
| WO | 9217118 A1 | 10/1992 |
| WO | 9301768 A1 | 2/1993 |
| WO | 9829057 | 7/1998 |
| WO | 9940964 A1 | 8/1999 |
| WO | 9947075 A1 | 9/1999 |
| WO | 2000018333 A1 | 4/2000 |
| WO | 2000030550 A1 | 6/2000 |
| WO | 2000041652 | 7/2000 |
| WO | 2000047139 A1 | 8/2000 |
| WO | 2001035878 A2 | 5/2001 |
| WO | 200149213 A2 | 7/2001 |
| WO | 0156512 A1 | 8/2001 |
| WO | 2001054624 A1 | 8/2001 |
| WO | 2001054625 A1 | 8/2001 |
| WO | 2001061289 A1 | 8/2001 |
| WO | 0176510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 0236048 A1 | 5/2002 |
| WO | 2002041789 A2 | 5/2002 |
| WO | 2002043620 A1 | 6/2002 |
| WO | 2002049540 A2 | 6/2002 |
| WO | 02076348 A1 | 10/2002 |
| WO | 2003003943 A2 | 1/2003 |
| WO | 2003030776 A2 | 4/2003 |
| WO | 03047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |

(56) References Cited

FOREIGN PATENT DOCUMENTS

| | | |
|---|---|---|
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013028387 A2 | 2/2013 |
| WO | 2013045262 A1 | 4/2013 |
| WO | 2013059747 A1 | 4/2013 |
| WO | 2013096411 A1 | 6/2013 |
| WO | 2013096757 A1 | 6/2013 |
| WO | 2013116785 A1 | 8/2013 |
| WO | 2013175468 A2 | 11/2013 |
| WO | 2014121280 A2 | 8/2014 |
| WO | 2014138284 A1 | 9/2014 |
| WO | 2014144020 A1 | 9/2014 |
| WO | 2014144937 A2 | 9/2014 |
| WO | 2014162306 A2 | 10/2014 |
| WO | 2014189974 A1 | 11/2014 |
| WO | 2014194178 A1 | 12/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

International Search Report for Appln. No. PCT/US2021/040996 dated Oct. 21, 2021. (3 pages).
"Shape Memory Alloys," Retrieved from the Internet: <http://webdocs.cs.ualberta.ca/~database/MEMS/sma.html>, Feb. 5, 2016, 3 pages.
"Shape Memory Alloys," Retrieved from the Internet: <http://webdocs.es.ualberta.ca/.about.database/MEMS/sma.html>, Nov. 14, 2012, 3 pages.
Al Zaibag, Muayed, et al., "Percutaneous Balloon Valvotomy in Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Australian Search Report for Application No. AU 2016215197 dated Sep. 12, 2019.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration In Dilated Hearts," Interactive Cardiovascular and Thoracic Surgery, 2005, 4:475-477.
Chamberlain, G., "Ceramics Replace Body Parts," Design News, Jun. 9, 1997, Issue 11, vol. 52, 5 pages.
Chinese Search Report for CN Application No. 201680013223.9, dated Oct. 29, 2018.
Choo, S. J. et al., "Aortic Root Geometry: Pattern of Differences Between Leaflets and Sinuses of Valsava," The Journal of Heart Valve Disease, Jul. 1999, 8:407-415.
Cullen, et al., "Transvenous, Antegrade Melody Valve-in-Valve Implantation for Bioprosthetic Mitral and Tricuspid Valve Dysfunction", JACC: Cardiovascular Interventions, vol. 6, No. 6, Jun. 2013, pp. 598-605.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Gray, H., The Aorta, Anatomy of the Human Body, 1918, Retrieved from the Internet <http://www.bartleby.com/107/142.html>, Oct. 12, 2012, 5 pages.
Gray, H., The Heart, Anatomy of the Human Body, 1918, Retrieved from the Internet <http://education.yahoo.com/reference/gray/subjects/subject/138>, Oct. 8, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Inoue, K. et al., "Clinical Application of Transvenous Mitral Commissurotomy by a New Balloon Catheter," The Journal of Thoracic and Cardiovascular Surgery, 1984, 87:394-402.
International Search Report and Written Opinion for International Application No. PCT/US2016/012305, dated Aug. 3, 2016, 18 pages.
International Search Report and Written Opinion for International Application No. PCT/US2016/016567, dated Aug. 3, 2016, 17 pages.
Jin, X. Y. et al., "Aortic Root Geometry and Stentless Porcine Valve Competence," Seminars in Thoracic and Cardiovascular Surgery, Oct. 1999, 11(4):145-150.

(56) References Cited

OTHER PUBLICATIONS

Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.

Kolata, G., "Device That Opens Clogged Arteries Gets a Failing Grade in a New Study," New York Times [online], <http://www.nytimes.com/1991/01/03/health/device-that-opens-clogged-ar- teries-gets-a-faili . . . ,>, published Jan. 3, 1991,retrieved from the Internet on Feb. 5, 2016, 3 pages.

Lawrence, D. D., "Percutaneous Endovascular Graft: Experimental Evaluation," Radiology, 1987, 163:357-360.

Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.

Lutter, G. et al., "Mitral Valved Stent Implantation," European Journal of Cardia-Thoracic Surgery, 2010, 38:350-355, 2 pages.

Ma, L. et al., "Double-crowned valved stents for off-pump mitral valve replacement," European Journal of Cardio-Thoracic Surgery, Aug. 2005, 28(2): 194-198.

Moazami, N. et al., "Transluminal aortic valve placement: A feasibility study with a newly designed collapsible aortic valve," ASAIO Journal, Sep./ Oct. 1996, 42(5):M381-M385.

Orton, C., "Mitralseal: Hybrid Transcatheter Mitral Valve Replacement," Symposium: Small Animal Proceedings, 2011, pp. 311-312.

Pavcnik, D. et al. "Development and Initial Experimental Evaluation of a Prosthetic Aortic Valve for Transcatheter Placement," Radiology, 1992; 183:151-154.

Porstmann, W. et al., "Der Verschlul?. des Ductus Arteriosus Persistens ohne Thorakotomie," Thoraxchirurgie Vaskulare Chirurgie, Band 15, Heft 2, Stuttgart, Apr. 1967, pp. 199-203.

Rashkind, W. J., "Creation of an Atrial Septal Defect Without Thoracotomy," The Journal of the American Medical Association, Jun. 13, 1966, 196( 11 ): 173-174.

Rashkind, W. J., "Historical Aspects of Interventional Cardiology: Past, Present, Future," Texas Heart Institute Journal, Dec. 1986, 13(4):363-367.

Reul, H. et al., "The Geomety of the Aortic Root in Health, at Valve Disease and After Valve Replacement," J. Biomechanics, 1990, 23(2):181-191.

Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.

Rosch, J. et al., "The Birth, Early Years and Future of Interventional Radiology," J Vasc Interv Radiol., Jul. 2003, 4:841-853.

Ross, D. N., "Aortic Valve Surgery," Guy's Hospital, London, 1968, pp. 192-197.

Rousseau, E. P. M et al., "A Mechanical Analysis of the Closed Hancock Heart Valve Prosthesis," Journal of Biomechanics, 1998, 21(7):545-562.

Sabbah, A. N. et al., "Mechanical Factors in the Degeneration of Porcine Bioprosthetic Valves: An Overview," Dec. 1989, Journal of Cardiac Surgery, 4(4):302-309.

Search Report from Chinese Office Action dated Jan. 19, 2020 for CN201680013223.9; 2 pages.

Selby, M.D., J. Bayne, "Experience with New Retrieval Forceps for Foreign Body Removal in the Vascular, Urinary, and Biliary Systems," Radiology 1990; 176:535-538.

Serruys, P.W., et al., "Stenting of Coronary Arteries. Are we the Sorcerer's Apprentice?," European Heart Journal (1989) 10, 774-782, pp. 37-45, Jun. 13, 1989.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, Barry T., et al., "Modifications of Gianturco Expandable Wire Stents," AJR:150, May 1988, Dec. 3, 1987, pp. 1185-1187.

U.S. Pat. No. 9,155,620, Oct. 2015, Gross et al. (withdrawn).

Watt, A.H., et al. "Inliavenous Adenosine in the Treatment of Supraventricular Tachycardia; a Dose-Ranging Study and Interaction with Dipyridamole," British Journal of Clinical Pharmacology (1986), 21, pp. 227-230.

Webb, J. G. et al., "Percutaneous Aortic Valve Implantation Retrograde from the Femoral Artery," Circulation, 2006, 113:842-850.

Wheatley, M.D., David J., "Valve Prostheses," Rob & Smith's Operative Surgery, Fourth Edition, pp. 415-424, ButtenNorths 1986.

Yoganathan, A. P. et al., "The Current Status of Prosthetic Heart Valves," In Polymetric Materials and Artificial Organs, Mar. 20, 1983, pp. 111-150, American Chemical Society.

\* cited by examiner

FULLY-TRANSSEPTAL APICAL PAD WITH PULLEY FOR TENSIONING

CROSS-REFERENCE TO RELATED APPLICATIONS

This application claims the benefit of the filing date of United States Provisional Patent Application No. 63/067,538 filed on Aug. 19, 2020 the disclosure of which is hereby incorporated herein by reference.

BACKGROUND OF THE DISCLOSURE

The present disclosure relates to collapsible and expandable prosthetic heart valves, and more particularly, to apparatus and methods for stabilizing a collapsible and expandable prosthetic heart valve within a native annulus of a patient.

Prosthetic heart valves that are collapsible to a relatively small circumferential size can be delivered into a patient less invasively than valves that are not collapsible. For example, a collapsible and expandable valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible and expandable prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed to reduce its circumferential size.

When a collapsed prosthetic valve has reached the desired implant site in the patient (e.g., at or near the native annulus of the patient's heart valve that is to be repaired by the prosthetic valve), the prosthetic valve can be deployed or released from the delivery apparatus and expanded to its full operating size. For balloon-expandable valves, this generally involves releasing the entire valve, assuring its proper location, and then expanding a balloon positioned within the valve stent. For self-expanding valves, on the other hand, the stent automatically expands as the stent is withdrawn from the delivery apparatus.

The clinical success of collapsible and expandable heart valves is dependent, in part, on the anchoring of the valve within the native annulus. Self-expanding valves typically rely on the radial force exerted by expanding the stent against the native annulus to anchor the prosthetic heart valve. However, if the radial force is too high, the heart tissue may be damaged. If, instead, the radial force is too low, the heart valve may move from its deployed position and/or migrate from the native annulus, for example, into the left ventricle.

Movement of the prosthetic heart valve may result in the leakage of blood between the prosthetic heart valve and the native valve annulus. This phenomena is commonly referred to as paravalvular leakage. In mitral valves, paravalvular leakage enables blood to flow from the left ventricle back into the left atrium during systole, resulting in reduced cardiac efficiency and strain on the heart muscle.

Anchoring prosthetic heart valves within the native valve annulus of a patient, especially within the native mitral valve annulus, can be difficult. For example, prosthetic mitral valves often require a low profile so as not to interfere with atrial function, and the low profile complicates securely anchoring the prosthetic heart valve in place. Moreover, the native mitral valve annulus has reduced calcification or plaque compared to the native aortic valve annulus, for example, which can make for a less stable surface to anchor the prosthetic heart valve. For this reason, collapsible and expandable prosthetic mitral valves often include additional anchoring features such as a tether. The tether is commonly secured to an apical pad that anchors the prosthetic heart valve in position within the native annulus of the patient.

Despite the improvements that have been made to anchoring collapsible and expandable prosthetic heart valves, shortcomings remain. For example, the apical pad is typically inserted through an incision made between the ribs of the patient and secured to an external surface at the apex of the heart. Conventional apical pads therefore require that the incision be of a sufficient size to allow the apical pad to be inserted through the incision before the tether is tensioned and fastened to the apical pad.

BRIEF SUMMARY OF THE DISCLOSURE

In accordance with a first aspect of the present disclosure, an expandable apical pad is provided. Among other advantages, the apical pad is designed to be collapsed to a delivery condition, loaded within a catheter along with the prosthetic heart valve and delivered to an implant site within the heart before the apical pad is extended through the ventricular wall of the heart, transitioned to an expanded deployed condition and secured to the apex of the heart. As a result, the apical pad disclosed herein may be delivered and secured to the heart in a less invasive manner than apical pads that are not collapsible.

One embodiment of the apical pad includes a first collar, a second collar and a plurality of struts extending between the first collar and the second collar. The plurality of struts have a delivery condition and a deployed condition. When the plurality of struts are in the delivery condition, the plurality of struts collectively form a first cross-section and when the plurality of struts are in the deployed condition, the plurality of struts collectively form a second cross-section greater than the first cross-section.

A prosthetic heart valve connectable to an apical pad is also provided herein and includes a collapsible and expandable support stent having an inflow end and an outflow end, a valve assembly disposed within the support stent, the valve assembly including a cuff and a plurality of leaflets, and a tether having a first end attached to the support stent and a second end. The apical pad includes a first collar, a second collar and plurality of struts extending between the first collar and the second collar. The plurality of struts have a delivery condition in which the plurality of struts collectively form a first cross-section and a deployed condition in which the plurality of struts collectively form a second cross-section greater than the first cross-section. The tether is preferably connected to the apical pad such that tensioning the tether transitions the plurality of struts from the delivery condition to the deployed condition.

A method of implanting a prosthetic heart valve within a native heart valve annulus is provided herein and includes delivering a delivery device to a target site adjacent to a native valve annulus while the delivering device holds an apical pad in a delivery condition and a prosthetic heart valve including a stent, a valve assembly disposed within the stent and a tether attached to the stent and to the apical pad; deploying the prosthetic heart valve from the delivery device within the native valve annulus; creating a passage through the wall of the heart; deploying the apical pad from the delivery device, through the passage to a location outside the heart; transitioning the apical pad from the delivery condition in which the apical pad has a first cross-section to a deployed condition in which the apical pad has a second cross-section greater than the first cross-section; and securing the apical pad against an external surface of the heart.

BRIEF DESCRIPTION OF THE DRAWINGS

Various embodiments of the present disclosure are described herein with reference to the drawings, wherein.

DETAILED DESCRIPTION

Blood flows through the mitral valve from the left atrium to the left ventricle. As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. Also as used herein, the terms "substantially," "generally," and "about" are intended to mean that slight deviations from absolute are included within the scope of the term so modified.

Figure 1:
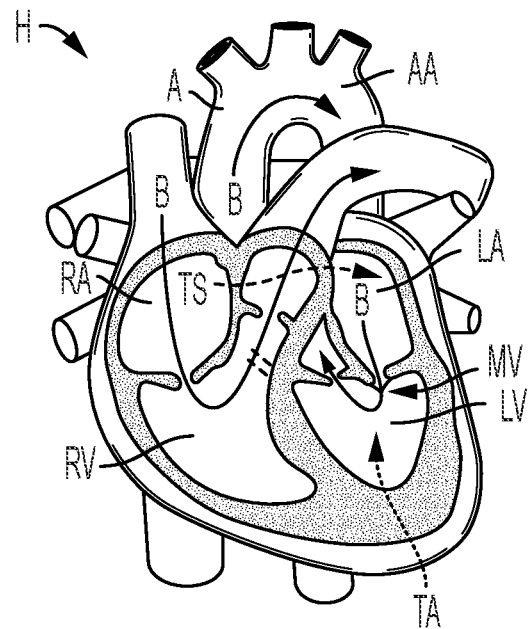
FIG. 1 is a highly schematic cutaway view of the human heart, showing two approaches for delivering a prosthetic mitral valve.

FIG. 1 is a schematic cutaway representation of a human heart H. The human heart includes two atria and two ventricles: right atrium RA and left atrium LA, and right ventricle RV and left ventricle LV. Heart H further includes aorta A and aortic arch AA. Disposed between the left atrium and the left ventricle is mitral valve MV. The mitral valve, also known as the bicuspid valve or left atrioventricular valve, is a dual-flap that opens as a result of increased pressure in left atrium LA as it fills with blood. As atrial pressure increases above that in left ventricle LV, mitral valve MV opens and blood flows into the left ventricle. Blood flows through heart H in the direction shown by arrows "B".

A dashed arrow, labeled "TA", indicates a transapical approach of implanting a prosthetic heart valve, in this case to replace the mitral valve. In the transapical approach, a small incision is made between the ribs of the patient and into the apex of left ventricle LV to deliver the prosthetic heart valve to the target site. A second dashed arrow, labeled "TS", indicates a transseptal approach of implanting a prosthetic heart valve in which the valve is inserted into the femoral vein and passed through the septum between right atrium RA and left atrium LA. Other approaches for implanting a prosthetic heart valve are also possible and may be used to implant the collapsible prosthetic heart valve described in the present disclosure.

Figure 2:
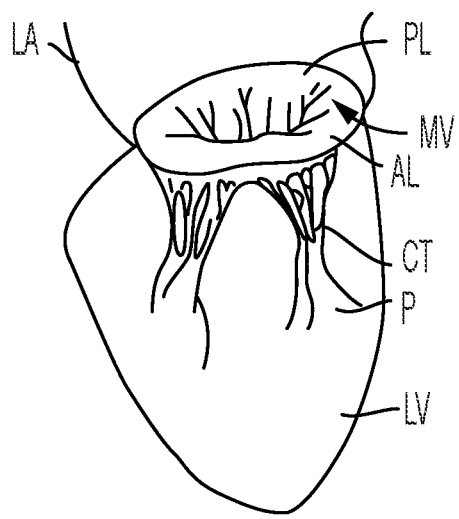
FIG. 2 is a highly schematic representation of a native mitral valve and associated cardiac structures.

FIG. 2 is a more detailed schematic representation of native mitral valve MV and its associated structures. As previously noted, mitral valve MV includes two flaps or leaflets, posterior leaflet PL and anterior leaflet AL, disposed between left atrium LA and left ventricle LV. Cord-like tendons, known as chordae-tendineae CT, connect the two leaflets to the medial and lateral papillary muscles P. During atrial systole, blood flows from higher pressure in left atrium LA to lower pressure in left ventricle LV. When left ventricle LV contracts during ventricular systole, the increased blood pressure in the chamber pushes the posterior and anterior leaflets to close, preventing the backflow of blood into left atrium LA. Since the blood pressure in left atrium LA is much lower than that in left ventricle LV, the leaflets attempt to evert to low pressure regions. Chordae tendineae CT prevent the eversion by becoming tense, thus pulling on the leaflets and holding them in the closed position.

Figure 3:
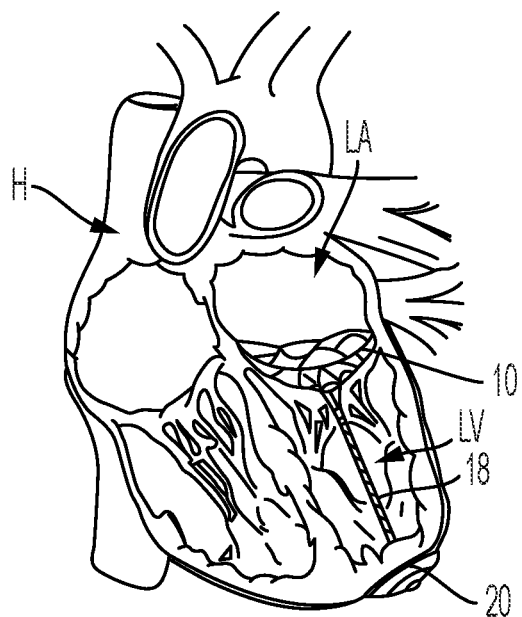
FIG. 3 is a highly schematic cutaway view of the human heart showing a collapsible and expandable prosthetic heart valve according to the prior art anchored within the native mitral annulus by a tether and an apical pad.

FIG. 3 illustrates a known collapsible and expandable prosthetic heart valve 10 secured within the native mitral valve annulus of a patient. For balloon-expandable variants, prosthetic heart valve 10 may be expandable, but not collapsible, or not readily collapsible, once expanded. When used to replace native mitral valve MV, prosthetic valve 10 may have a low profile so as not to interfere with the heart's electrical conduction system pathways or the atrial function.

Figure 4A:
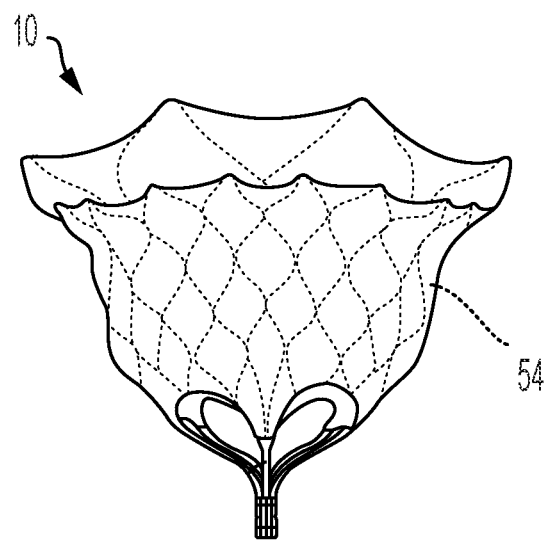
FIG. 4A is a side elevational view of the prosthetic mitral valve of FIG. 3.
Figure 4B:
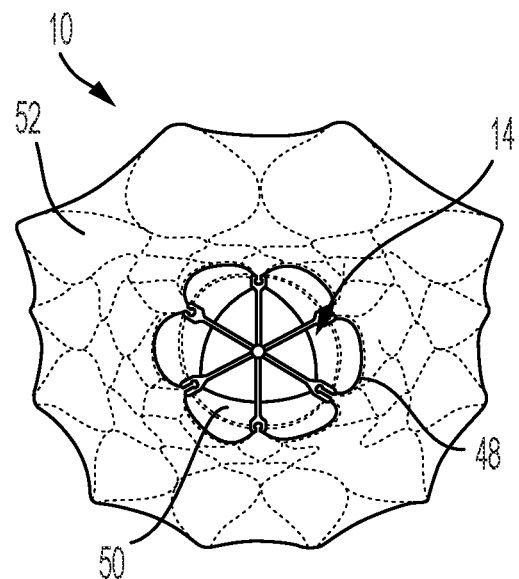
FIG. 4B is a plan view of the prosthetic mitral valve of FIG. 3.
Figure 4C:
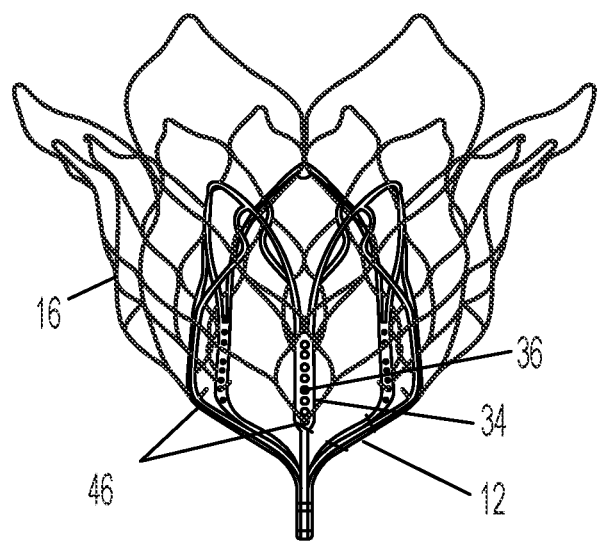
FIG. 4C is a side elevational view showing an inner stent disposed within and secured to an outer stent of the prosthetic mitral valve of FIG. 3.

With continued reference to FIG. 3 and further reference to FIGS. 4A-4C, prosthetic heart valve 10 includes an inner stent 12 securing a valve assembly 14, an outer stent 16 secured to and disposed around the inner stent and a tether 18 configured to be secured to an apical pad 20. Both the inner stent 12 and the outer stent 16 may be formed from biocompatible materials that are capable of self-expansion, for example, shape-memory alloys such as nitinol. Alternatively, inner stent 12 or outer stent 16 may be balloon expandable or expandable by another force exerted radially outward on the stent. When expanded, outer stent 16 may exert an outwardly directed radial force against the native valve annulus that assists in anchoring inner stent 12 and valve assembly 14 within the native annulus.

Figure 5A:
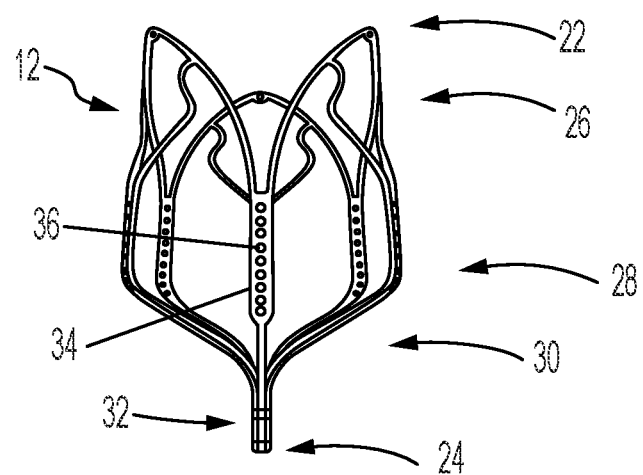
FIG. 5A is a side elevational view of the inner stent of FIG. 4C.

Referring to FIG. 5A, inner stent 12 extends along a longitudinal axis between an inflow end 22 and an outflow end 24. In one example, inner stent 12 is formed by laser cutting a predetermined pattern into a metallic tube, such as a self-expanding tube formed of a shape-memory alloy such as nitinol, to form four portions: cusps 26, a body portion 28, a strut portion 30 and a tether clamp 32 that clamps and secures tether 18 (shown in FIG. 3).

Strut portion 30 may include, for example, six struts that extend radially inward from body portion 28 to tether clamp 32. When inner stent 12 is expanded, strut portion 30 forms a radial transition between body portion 28 and tether clamp 32 that facilitates crimping of the inner stent when tether 18 is retracted within a delivery device. Body portion 28 may also include six longitudinal posts 34 having a plurality of bores or eyelets 36 for securing valve assembly 14 to the inner stent 12 by one or more sutures. As shown in FIG. 5A, three cusps 26 are positioned at the inflow end 22 of inner stent 12. Each of cusps 26 is circumferentially disposed between a pair of adjacent longitudinal posts 34.

Figure 5B:
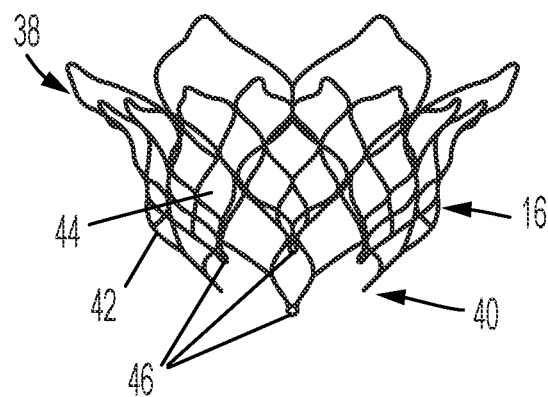
FIG. 5B is a side elevational view of the outer stent of FIG. 4C.

Outer stent 16, shown in FIG. 5B, extends along the longitudinal axis between an atrial end 38 and a ventricular end 40. Outer stent 16 may include a plurality of struts 42 that form cells 44 extending about the outer stent in one or more annular rows. In one example, outer stent 16 is formed by laser cutting a predetermined pattern into a metallic tube, such as a self-expanding nitinol tube. Cells 44 may be substantially the same size around the perimeter of stent 16 and along the length of the stent. Alternatively, cells 44 near the atrial end 38 of outer stent 16 may be larger than the cells near the ventricular end 40. When outer stent 16 is expanded, the struts 42 forming a cell 44 in the annular row of cells adjacent the atrial end 38 of the outer stent may bend about the midsection of the cell (e.g., in a direction generally orthogonal to the longitudinal axis) such that the upper apex of the cell extends radially outward relative to the midsection of the cell and forms an atrial flange. When prosthetic valve 10 is disposed within a native mitral valve MV, the flange is designed to protrude into the left atrium LA and engage an upper surface of the native mitral valve annulus to form a seal and prevent blood from flowing between the prosthetic valve and the native annulus.

A plurality of attachment features 46 may lie at the intersections of the struts 42 that form the cells 44 at the ventricular end 40 of outer stent 16. Attachment features 46 may include an eyelet that facilitates the suturing of outer stent 16 to the longitudinal posts 34 of inner stent 12 thereby securing the inner and outer stents together as shown in FIG. 4C. In one example, each attachment feature 46 may be sutured to a single eyelet 36 of longitudinal post 34, proximate to the outflow end 24 of inner stent 12 such that outer stent 16 may evert relative to and about the inner stent as is described in more detail below with reference to FIGS. 6A and 6B.

Referring back to FIGS. 4A and 4B, valve assembly 14 may be secured to inner stent 12 by suturing the valve assembly to longitudinal posts 34. Valve assembly 14 includes a cuff 48 and a plurality of leaflets 50 that open and close collectively to function as a one-way valve. The eyelets 36 of longitudinal posts 34 facilitate the suturing of the leaflet commissure to the body portion 28 of inner stent 12. Cuff 48 and leaflets 50 may be wholly or partly formed of any suitable biological material, such as bovine or porcine pericardium, or biocompatible polymer, such as polytetrafluoroethylene (PTFE), urethanes and the like.

An inner skirt 52 may be disposed on a luminal surface of outer stent 16. Inner skirt 52 may also be formed of any suitable biological material, such as bovine or porcine pericardium, or biocompatible polymer, such as PTFE, urethanes or similar materials. An outer skirt 54 may be disposed about an abluminal surface of outer stent 16. Outer skirt 54 may be formed of a polyester fabric that promotes tissue ingrowth.

Figure 6A:
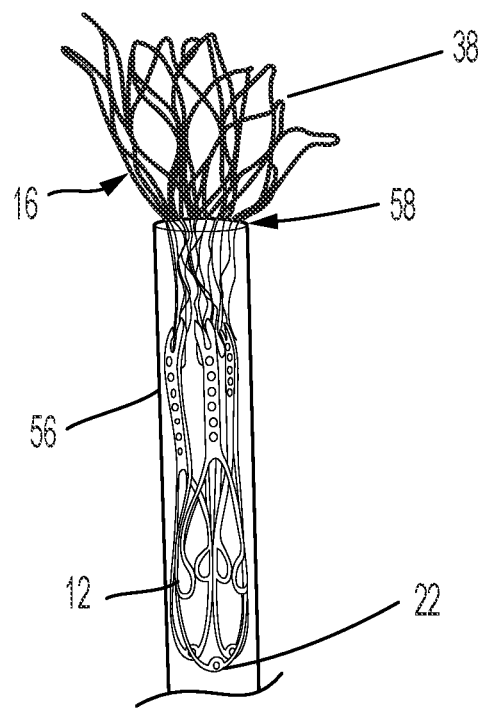
FIGS. 6A and 6B are highly schematic partial views of a delivery catheter deploying the prosthetic mitral valve of FIG. 3.
Figure 6B:
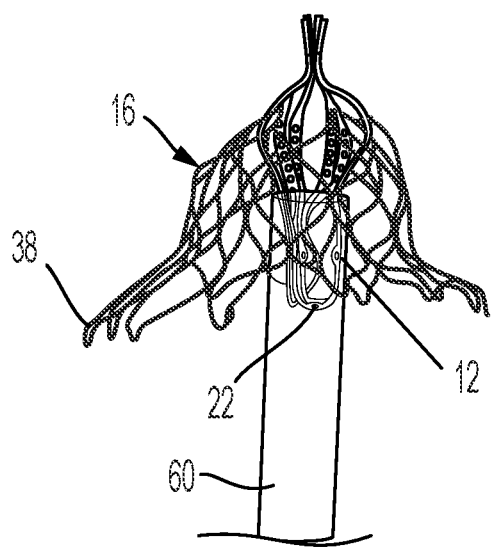

Prosthetic heart valve 10 may be used to repair a malfunctioning native heart valve, such as a native mitral valve, or a previously implanted and malfunctioning prosthetic heart valve. In embodiments in which outer stent 16 is designed to evert, prosthetic heart valve 10 may be collapsed and loaded within a delivery device 56 such that the atrial end 38 of outer stent 16 faces a leading end 58 of the delivery device and the inflow end 22 of inner stent 12 faces a trailing end (not shown) of the delivery device as shown in FIG. 6A. Delivery device 56 may then be percutaneously introduced into the patient and delivered to a desired implant site at or near the native mitral annulus.

Once delivery device 56 has reached the target site, a physician may unsheathe prosthetic heart valve 10 to first allow the outer stent 16 to expand from the collapsed condition and evert about inner stent 12 as the outer stent expands and engages the native valve annulus. Further unsheathing of prosthetic heart valve 10 will allow the inner stent 12 to expand from the collapsed condition to the expanded condition within the anchored outer stent 16 and allow the leaflets 50 to act as a one-way valve. The physician may then make an incision between the ribs of the patient and into the apex of left ventricle LV. After the incision has been made, tether 18 may be pulled through the incision so that the tether extends out from the left ventricle LV of the heart. Apical pad 20 may then be inserted through the incision and placed against an external surface of the apex before the tether is tensioned and secured to the apical pad as shown in FIG. 3. It will be appreciated that the incision must be of sufficient size to allow apical pad 20 to be inserted through the incision and fastened to the heart to anchor prosthetic valve 10 within the native valve annulus. An apical pad that can be secured to the heart through smaller incisions to reduce the invasiveness of the valve repair procedure is desired.

Figure 7A:
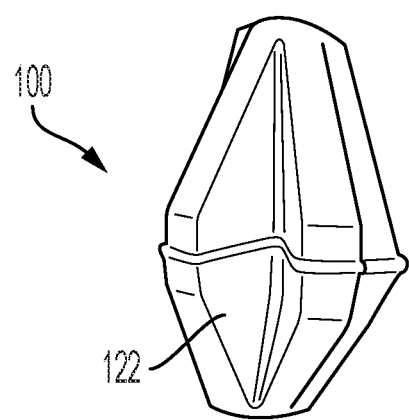
FIG. 7A is a side elevational view of an apical pad having a fabric covering in an elongated delivery condition according to an embodiment of the present disclosure.
Figure 7B:
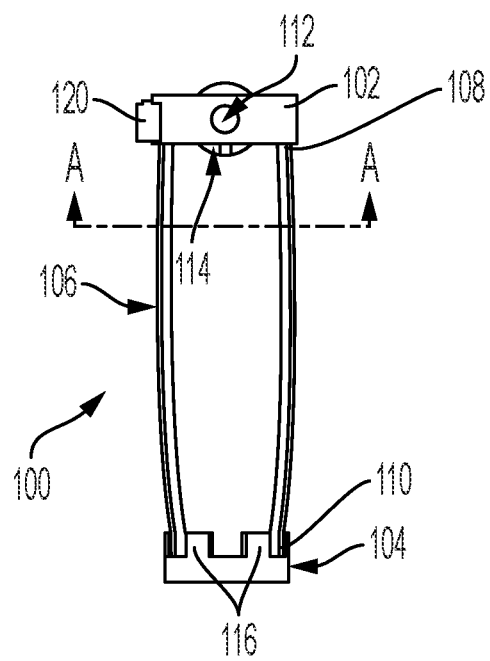
FIG. 7B is a side elevational view of the apical pad of FIG. 7A without the fabric covering.

FIGS. 7A and 7B illustrate a collapsible and expandable apical pad 100 according to an embodiment of the present disclosure. Apical pad 100 is radially collapsible to a delivery condition in which the apical pad can be loaded within a delivery device and percutaneously delivered to the heart of a patient and subsequently expanded to a deployed condition in which the apical pad may be fastened to the apex of the heart. The collapsibility of apical pad 100 allows it to be delivered into the body of a patient in a less invasive manner than conventional apical pad 20 (described above with reference to FIG. 3). Although apical pad 100 is described herein as a replacement for apical pad 20, it will be appreciated that apical pad 100 may be attached to the tether of any prosthetic heart valve and used in the repair of the native mitral valve of a patient or another cardiac valve such as the aortic valve.

Apical pad 100 includes a first collar 102, a second collar 104 and a plurality of struts 106. In one embodiment, apical pad 100 is formed by laser cutting a predetermined pattern into a metallic tube formed of biocompatible materials capable of self-expansion, for example, shape-memory alloys such as nitinol. The mechanical properties of the shape-memory alloys provide struts 106 the ability to compress and expand, thus, transitioning apical pad 100 between an elongated condition (FIG. 7B) (e.g., a delivery condition) and a radially expanded condition (FIG. 8) (e.g., a deployed condition). The struts 106 of apical pad 100 may be heat-set, or otherwise preset, to the radially expanded condition. In this regard, once apical pad 100 is released from a delivery device, such as delivery device 56, struts 106 will expand to their preset configuration and cause the apical pad to transition to its deployed configuration.

Each one of the plurality of struts 106 extends generally in the longitudinal direction of the apical pad from a first end 108 attached to first collar 102 to a second end 110 attached to the second collar 104 and couples the first and second collars to one another. When struts 106 are longitudinally compressed and radially expanded, first collar 102 moves relatively towards second collar 104. On the other hand, when struts 106 are elongated in the longitudinal direction of the apical pad, first collar 102 moves away from second collar 104.

Figure 7C:
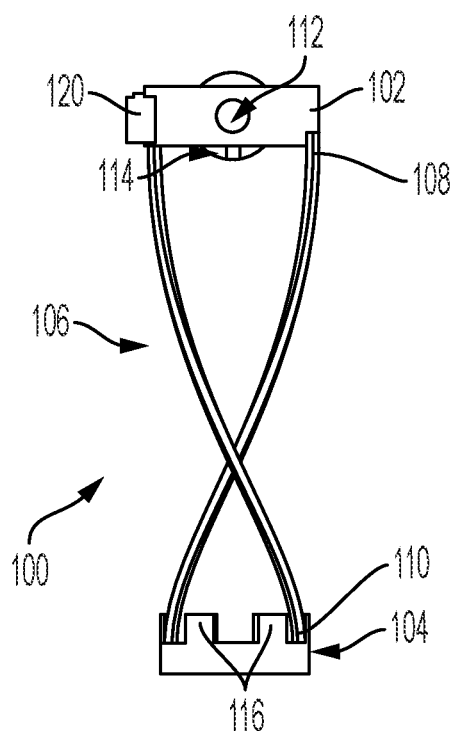
FIG. 7C is a side elevational view of an apical pad according to another embodiment of the present disclosure.

The first ends 108 of struts 106 are attached to first collar 102 at first attachment locations which may be annularly disposed about the first collar, while the second ends 110 of the struts are attached to second collar 104 at second attachment locations which may be annularly disposed about the second collar. In a preferred embodiment, as shown in FIG. 7C, each second attachment location is angularly offset from a respective first attachment location (e.g., the second attachment location of a strut is not aligned with the first attachment location of that strut in the longitudinal direction the apical pad). In other words, each strut 106 partially circumscribes the longitudinal axis of apical pad 100 between the first and second attachment locations. Preferably, each second attachment location is offset from the first attachment location in a circumferential direction about the longitudinal axis by an angle that may be determined by dividing 360 degrees by the number of struts 106. For example, because two struts 106 are illustrated in FIG. 7C, each second attachment location is illustrated as being offset 180 degrees from a respective first attachment location. In this manner, struts 106 collectively circumscribe the longitudinal axis of the apical pad 100 as the struts are longitudinally compressed and expanded outwardly in a radial direction of the apical pad. The compressed struts form an ellipse and expand padding 122 (FIGS. 7A and 11) in a radial direction. Padding 122 may be sewn to or otherwise coupled to struts 106 and may be formed from a polyester fabric or another material that facilitates the clotting of blood and the ingrowth of tissue. It is believed that the ellipse creates a superior seal because the ellipse completely circumscribes the longitudinal axis of apical pad 100 and, in turn, is configured to completely circumscribe a puncture extending through the wall of the heart to prevent the leakage of blood.

In a preferred embodiment, apical pad 100 has a cross-section that is approximately equal to or less than 24 French, and preferably equal to or less than 18 French, when struts 106 are in the longitudinally elongated delivery condition. In this manner, apical pad 100 can be loaded within a delivery device sized for transseptal delivery through the femoral artery. When struts 106 are longitudinally compressed and expanded in the radial direction, apical pad 100 may have a cross-section that is greater than 24 French.

Figure 9:
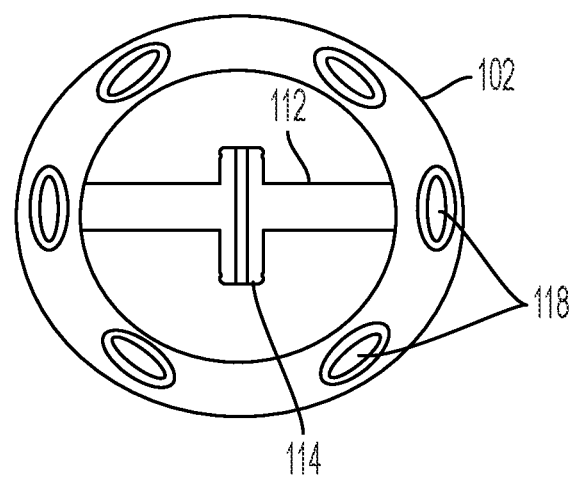
FIG. 9 is a cross-sectional view of the apical pad of FIG. 7B taken along line A-A.

With reference to FIGS. 7B, 7C and 9, first collar 102 may include a beam 112 extending generally orthogonal to the longitudinal axis of apical pad 100 and across the cross-section of the first collar. In one embodiment, beam 112 may be laser welded to first collar 102 after manufacturing the beam separately from first collar 102, second collar 104, and struts 106. A pulley 114 configured to receive tether 18, or the tether of an alternate embodiment of a prosthetic heart valve, may be rotatably secured to beam 112 such that apical pad 100 transitions from the delivery condition to the deployed condition when the tether is tensioned.

Second collar 104 may optionally include one or more locking tabs 116 extending away from a surface of the second collar that faces first collar 102. Each locking tab 116 is longitudinally aligned with a respective recess 118 defined in a surface of first collar 102 that faces second collar 104 such the locking tabs are configured to enter a respective recess and lock the first collar to the second collar when apical pad 100 is tensioned. In one embodiment, locking tabs 116 are sized to friction fit within recesses 118 and prevent first collar 102 from separating from second collar 104 after apical pad 100 has been tensioned to position the locking tabs within the recesses. Locking tabs 116 may alternatively include a rib-like shelf (not shown) to engage a corresponding groove disposed within recess 118 to lock first collar 102 and second collar 104 together. When second collar 104 includes a plurality of locking tabs 116, the locking tabs may be annularly spaced about the second collar such that one or more locking tabs are disposed between adjacent second attachment locations for the ends 110 of struts 106. It will be appreciated that locking tabs 116 may alternatively protrude from first collar 102 while recesses 118 may be formed in second collar 104. In some embodiments, alternative, or additional, locking features may be utilized to secure first collar 102 to second collar 104.

First collar 102 may further include a locking pin assembly 120 to secure tether 18. Locking pin assembly 120 may include a locking pin moveable through a pin channel defined in first locking collar 102 and extending orthogonally to the longitudinal axis of apical pad 100 such that the pin is configured to pierce or otherwise engage tensioned tether 18 against pulley 114 and prevent the tension from being released.

Figure 10:
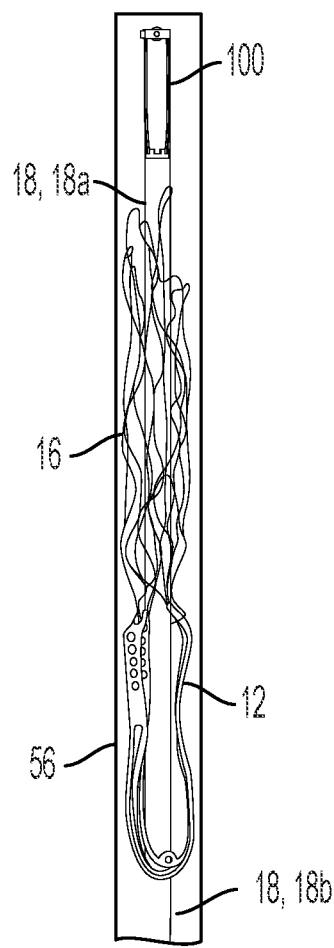
FIG. 10 is a highly schematic side elevational view showing a delivery catheter loaded with the apical pad of FIG. 7B and secured to the prosthetic mitral valve of FIG. 3.

Use of apical pad 100 to anchor prosthetic heart valve 10 within a native mitral valve annulus will now be described with reference to FIGS. 7A-11. With a first end of tether 18 secured to the clamp 32 of inner stent 12, a physician may take the free end of the tether and wrap it around the pulley 114 of apical pad 100 to couple prosthetic heart valve 10 and the apical pad to one another. The coupled prosthetic heart valve 10 and elongated apical pad 100 may then be loaded into delivery device 56. More particularly, outer stent 16 may be everted and prosthetic heart valve 10 may be collapsed and loaded within delivery device 56 such that the atrial end 38 of outer stent 16 faces the leading end 58 of the delivery device and the inflow end 22 of inner stent 12 faces the trailing end of the delivery device. Apical pad 100 may then be transitioned to the delivery condition and loaded into the leading end 58 of delivery device 56 such that the apical pad is disposed between prosthetic heart valve 10 and the leading end of the delivery device with the free end of the tether extending back towards the trailing end of the delivery device. In other words, as is shown in FIG. 10, after prosthetic heart valve 10 and apical pad 100 have been loaded within delivery device 56, a first portion 18a of the tether extends between the tether clamp 32 of inner stent 12 and the pulley 114 of the apical pad, and a second portion 18b of the tether extends from the pulley and out from the trailing end of the delivery device such that it can be manipulated by a physician.

Figure 8:
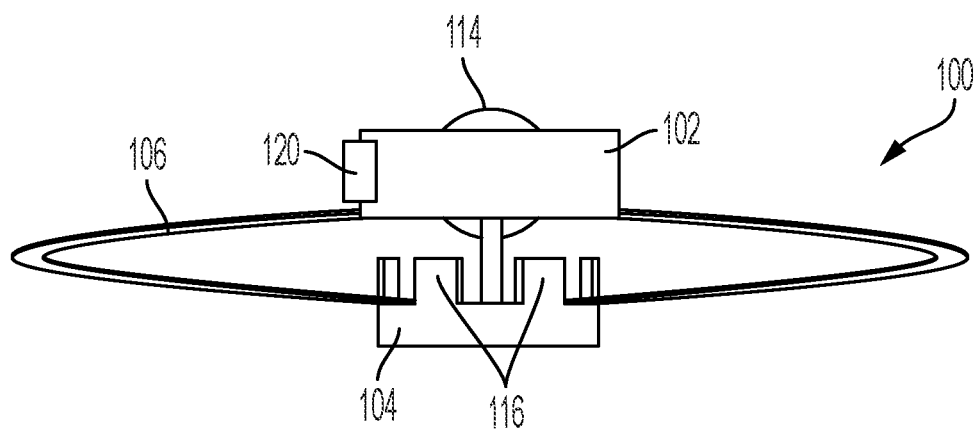
FIG. 8 is a side elevational view of the apical pad of FIG. 7C in a deployed condition.

Delivery device 56 may be percutaneously introduced into the patient, for example, via the femoral vein and delivered into the left ventricle LV using a transseptal approach. With the leading end 58 of delivery device 56 positioned within the left ventricle LV, the physician may use the leading end of the delivery device (or a separate cutting tool) to puncture through the myocardium at the apex of the heart. A plunger (not shown) may then be used to push apical pad 100 out from the leading end 58 of delivery device 56 and through the wall of the heart. The struts 106 of apical pad 100 may then naturally expand in the radial direction to their preset condition and cause the apical pad to the deployed condition as shown in FIG. 8.

Figure 11:
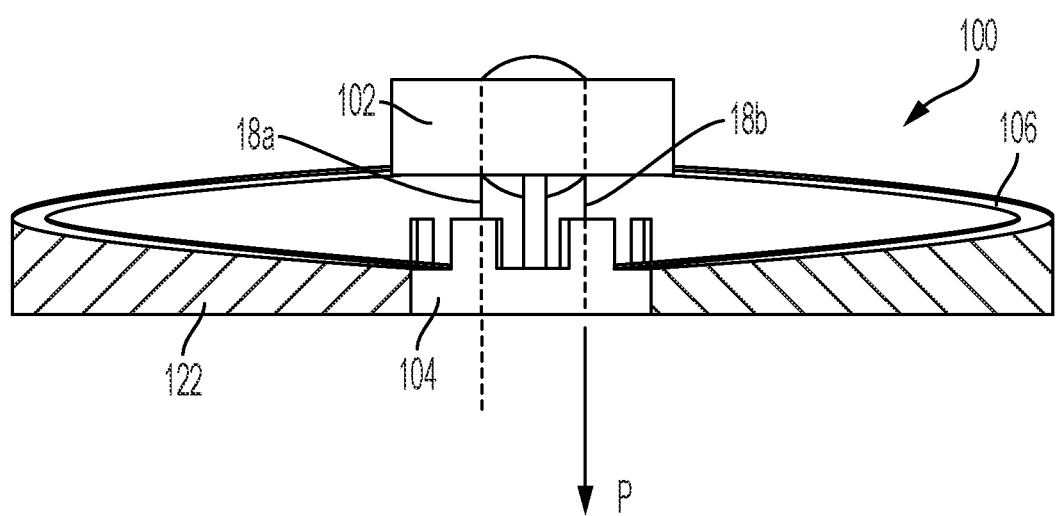
FIG. 11 is a highly schematic side elevational view illustrating the tensioning of a tether to transition the apical pad of FIG. 7C to the deployed condition.

The leading end 58 of delivery device 56 may then be retracted to a location within the left atrium and adjacent to the native mitral valve annulus. Once the leading end 58 of delivery device 56 has been properly positioned, the physician may unsheathe prosthetic heart valve 10 allowing outer stent 16 to evert about inner stent 12 within left atrium LA. The physician may then move the leading end 58 of delivery device 56 to a location within the native mitral valve annulus until the outer stent is properly positioned within the native valve annulus and the flange of the outer stent is engaged with an atrial side of the native annulus. Further unsheathing of prosthetic heart valve 10 will cause the inner stent 12 to expand from the collapsed condition to the expanded condition, within anchored outer stent 16, and allow the leaflets 50 to act as a one-way valve. After the physician has confirmed that prosthetic heart valve 10 has been properly positioned, and leaflets 50 are properly coapting, the physician may tension tether 18. As shown in FIG. 11, pulling the free end of tether 18 towards the trailing end of delivery device 56 (in the direction of the arrow labeled P) causes struts 106 to further compress in the longitudinal direction, and expand outwardly in the radial direction, such that the struts collectively form an ellipse about the longitudinal axis of apical pad 100. As struts 106 compress in the longitudinal direction of apical pad 100, first collar 102 moves relatively towards second collar 104 and, in embodiments in which the apical pad includes locking features, may allow locking tabs 116 to be positioned within recesses 118 to lock the first and second collars to one another and prevent the first and second collars from subsequently being separated.

The physician may then actuate locking pin assembly 120 to move the locking pin and to clamp the tether against the pulley 114, preventing the tether from releasing the tension. The physician may then cut the second portion 18b of the tether before removing the second portion and delivery device 56 from the patient. It will be appreciated that because apical pad 100 is expanded by tensioning tether 18, no incision between the patient's ribs need to be made. As a result, apical pad 100 allows for a less invasive valve repair procedure than apical pad 20.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, while the foregoing disclosure describes the struts forming an ellipse in the deployed condition, that is not necessarily the case. The struts in the deployed condition can form any number of shapes depending on the total number of struts in the apical pad and the angle between the first and second ends of the struts.

The invention claimed is:

1. An apical pad, comprising:
a first collar;
a second collar;
a plurality of struts extending between the first collar and the second collar, the plurality of struts having a delivery condition and a deployed condition, wherein when the plurality of struts are in the delivery condition, the plurality of struts collectively form a first cross-section and when the plurality of struts are in the deployed condition, the plurality of struts collectively form a second cross-section greater than the first cross-section; and
a pulley rotatably coupled to the first collar;
wherein the apical pad has a longitudinal axis extending from the first collar to the second collar, and the first collar further comprises a beam extending substantially orthogonal to the longitudinal axis, the pulley being rotatable about the beam.

2. The apical pad of claim 1, wherein the struts are formed of nitinol.

3. The apical pad of claim 1, wherein the first cross-section is equal to or less than approximately 24 French and the second cross-section is greater than 24 French.

4. An apical pad, comprising:
a first collar;
a second collar;
a plurality of struts extending between the first collar and the second collar, the plurality of struts having a delivery condition and a deployed condition, wherein when the plurality of struts are in the delivery condition, the plurality of struts collectively form a first cross-section and when the plurality of struts are in the deployed condition, the plurality of struts collectively form a second cross-section greater than the first cross-section; and
a locking tab projecting from at least one of the first collar or the second collar,
wherein the other one of the first collar or the second collar defines a recess configured to receive the locking tab and to lock the first collar to the second collar.

5. A prosthetic heart valve, comprising:
a collapsible and expandable support stent having an inflow end and an outflow end;
a valve assembly disposed within the support stent, the valve assembly including a cuff and a plurality of leaflets;
a tether having a first end attached to the support stent and a second end; and
an apical pad including a first collar, a second collar and plurality of struts extending between the first collar and the second collar, the plurality of struts having a delivery condition in which the plurality of struts collectively form a first cross-section and a deployed condition in which the plurality of struts collectively form a second cross-section greater than the first cross-section,
wherein the tether is connected to the apical pad such that tensioning the tether transitions the plurality of struts from the delivery condition to the deployed condition, and
wherein the prosthetic heart valve includes a valve delivery condition in which (i) the prosthetic heart valve is collapsed within a delivery device, (ii) the apical pad is collapsed within the delivery device with the plurality of struts in the delivery condition, and (iii) the tether is attached to the apical pad.

6. The prosthetic heart valve of claim 5, further comprising a pulley rotatably attached to the first collar.

7. The prosthetic heart valve of claim 5, wherein each of the plurality of struts includes a first end attached to the first collar at a first attachment location and a second end attached to the second collar at a second attachment location, and the first attachment location is offset from the second attachment location by an angle in a circumferential direction about the longitudinal axis.

8. The prosthetic heart valve of claim 7, wherein the plurality of struts includes a fixed number of struts and the angle is equal to 360 degrees divided by the fixed number of struts.

9. The prosthetic heart valve of claim 5, further comprising a plurality of locking tabs annularly spaced about one of the first collar or the second collar.

10. The prosthetic heart valve of claim 9, wherein a plurality of recesses are formed in the other one of the first collar or the second collar, each of the plurality of recesses being configured to receive a respective one of the locking tabs and to lock the first collar to the second collar.

11. The prosthetic heart valve of claim 5, wherein the apical pad further comprises a fabric material that promotes tissue ingrowth.

12. The prosthetic heart valve of claim 5, further comprising an expandable and collapsible anchoring stent having an atrial end and a ventricular end, the anchoring stent being coupled to and at least partially surrounding the support stent when the prosthetic heart valve is implanted within a native annulus of a patient.

\* \* \* \* \*